(12) United States Patent
Makeyev

(10) Patent No.: US 11,045,132 B1
(45) Date of Patent: Jun. 29, 2021

(54) CONCENTRIC RING ELECTRODES FOR IMPROVED ACCURACY OF LAPLACIAN ESTIMATION

(71) Applicant: Diné College, Tsaile, AZ (US)

(72) Inventor: Oleksandr Makeyev, Tsaile, AZ (US)

(73) Assignee: Diné College, Tsaile, AZ (US)

( * ) Notice: Subject to any disclaimer, the term of this patent is extended or adjusted under 35 U.S.C. 154(b) by 0 days.

(21) Appl. No.: 17/067,480

(22) Filed: Oct. 9, 2020

(51) Int. Cl.
*A61B 5/291* (2021.01)
(52) U.S. Cl.
CPC ...... *A61B 5/291* (2021.01); *A61B 2562/0209* (2013.01); *A61B 2562/0215* (2017.08); *A61B 2562/04* (2013.01)

(58) Field of Classification Search
CPC ............ A61B 5/291; A61B 2562/0215; A61B 2562/0209; A61B 2562/04
See application file for complete search history.

(56) References Cited

U.S. PATENT DOCUMENTS

| | | | |
|---|---|---|---|
| 7,043,292 B2 | 5/2006 | Tarjan et al. | |
| 8,190,248 B2 | 5/2012 | Besio et al. | |
| 8,352,012 B2 | 1/2013 | Besio | |
| 8,615,283 B2 | 12/2013 | Besio | |
| 8,626,259 B2 | 1/2014 | Besio | |
| 2012/0150011 A1* | 6/2012 | Besio | A61N 1/0502 600/388 |

FOREIGN PATENT DOCUMENTS

| | | | | |
|---|---|---|---|---|
| ES | 2425692 | * | 10/2013 | ............... A61B 5/04 |
| WO | 2013135931 A1 | | 9/2013 | |

OTHER PUBLICATIONS

Prats Boluda, Gema, Translation of ES2425692A1, "Device for Measuring Bioelectric Signals on the Surface of the Body, Based on Adjustable Ring Sensors", (Year: 2013),Translated on Jan. 7, 2021.*
Oleksandr Makeyev et. al., "Proof of concept Laplacian estimate derived for noninvasive tripolar concentric ring electrode with incorporated radius of the central disc and the widths of the concentric rings", retreived: Jan. 7, 2021,, (Year: 2017).*

(Continued)

*Primary Examiner* — Eun Hwa Kim
*Assistant Examiner* — Adam Z Minchella
(74) *Attorney, Agent, or Firm* — Kilpatrick Townsend & Stockton LLP

(57) ABSTRACT

An electrode device for electrophysiological measurement may include an electrode substrate having a surface area. The electrode device may include a central electrode disposed on the electrode substrate around a central portion of the surface area. The electrode device may include a plurality of electrodes disposed on the electrode substrate concentric with the central electrode. The plurality of electrodes may include a first electrode covering a first portion of the surface area of the electrode substrate and a second electrode covering a second portion of the surface area of the electrode substrate. The second portion may be greater than a combined surface area of the first portion and the central portion.

20 Claims, 10 Drawing Sheets

(56) References Cited

OTHER PUBLICATIONS

Oleksandr Makeyev, "Solving the general inter-ring distances optimization problem for concentric ring electrodes to improve Laplacian estimation", retrieved: Jan. 7, 2021, Published: Aug. 30, 2018, (Year: 2018).*

Prats Boluda, Gema, Translation of ES2425692A1, "Device for Measuring Bioelectric Signals on the Surface of the Body, Based on Adjustable Ring Sensors",, Translated on Jan. 7, 2021 (Year: 2013).*

Oleksandr Makeyev et. al., "Improving the Accuracy of Laplacian Estimation with Novel Variable Inter-Ring Distances Concentric Ring Electrodes", retrieved Apr. 27, 2021, Published: Jun. 10, 2016, (Year: 2016).*

\* cited by examiner

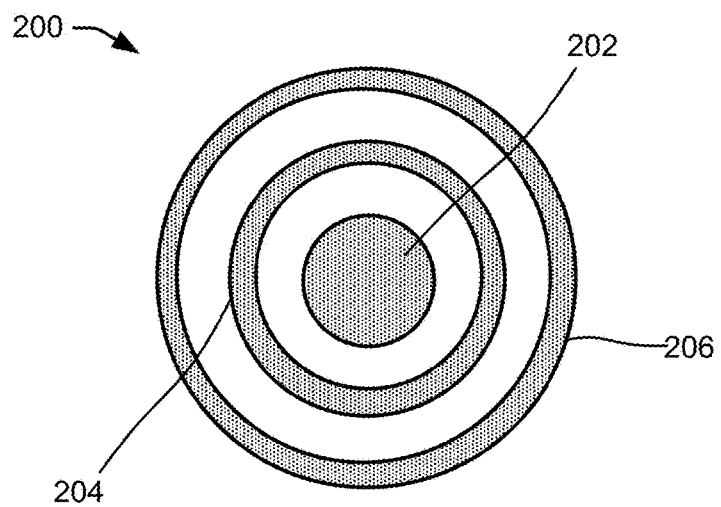
FIG. 2A
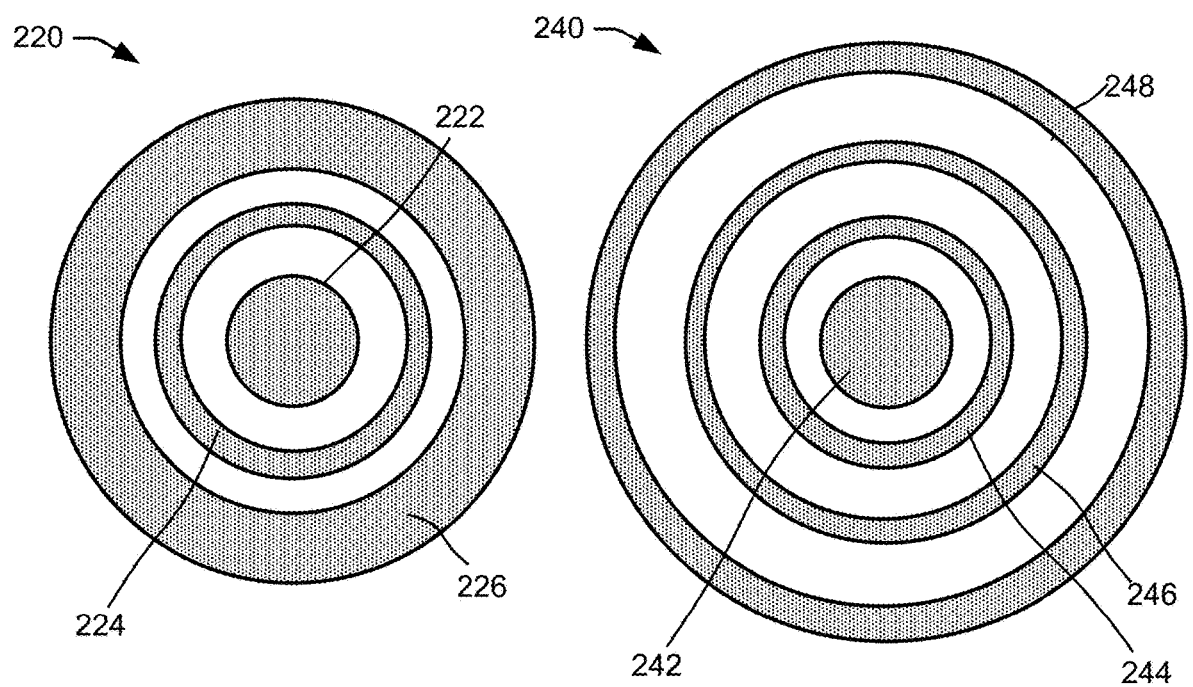
FIG. 2B
FIG. 2C

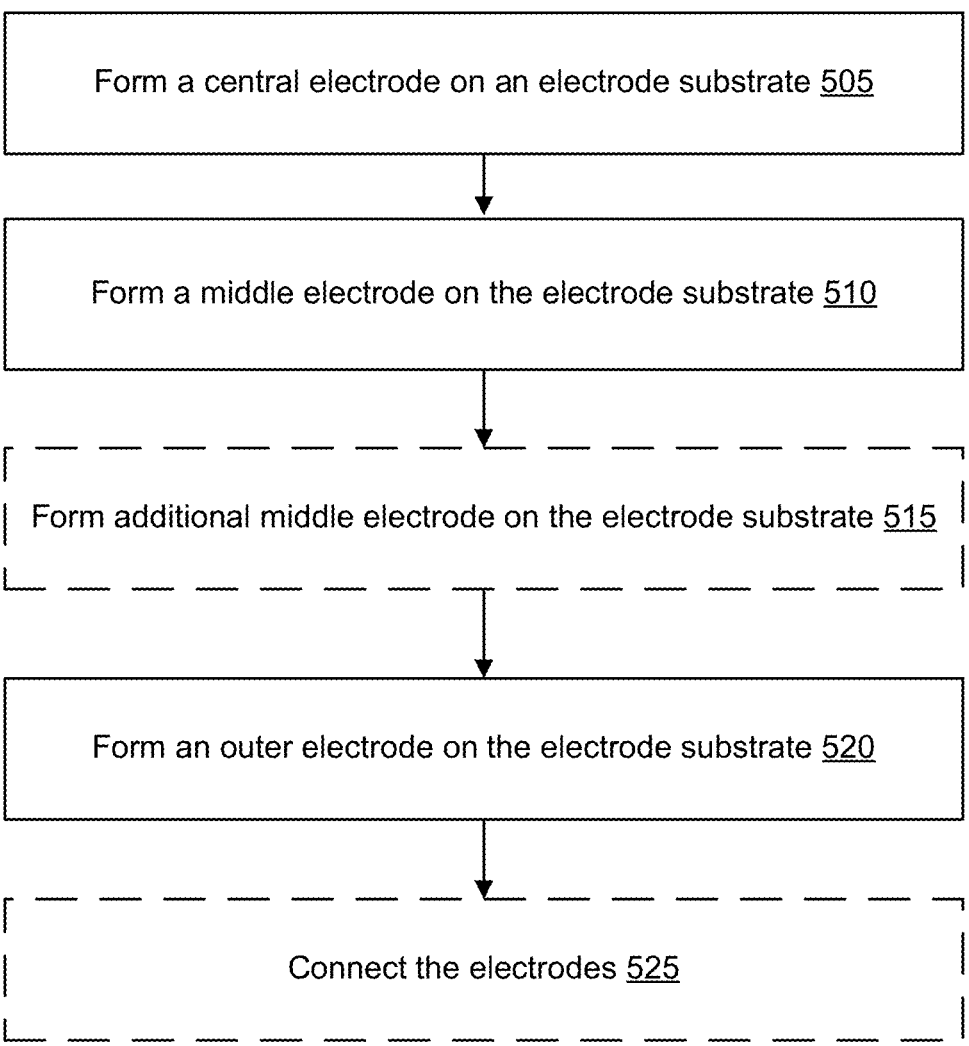

```
Form a central electrode on an electrode substrate 505
                            ↓
Form a middle electrode on the electrode substrate 510
                            ↓
┌ ─ ─ ─ ─ ─ ─ ─ ─ ─ ─ ─ ─ ─ ─ ─ ─ ─ ─ ─ ─ ─ ─ ─ ─ ─ ┐
│ Form additional middle electrode on the electrode substrate 515 │
└ ─ ─ ─ ─ ─ ─ ─ ─ ─ ─ ─ ─ ─ ─ ─ ─ ─ ─ ─ ─ ─ ─ ─ ─ ─ ┘
                            ↓
Form an outer electrode on the electrode substrate 520
                            ↓
┌ ─ ─ ─ ─ ─ ─ ─ ─ ─ ─ ─ ─ ─ ─ ─ ─ ─ ─ ─ ─ ─ ─ ─ ─ ─ ┐
│              Connect the electrodes 525                │
└ ─ ─ ─ ─ ─ ─ ─ ─ ─ ─ ─ ─ ─ ─ ─ ─ ─ ─ ─ ─ ─ ─ ─ ─ ─ ┘
```

FIG. 5

CONCENTRIC RING ELECTRODES FOR IMPROVED ACCURACY OF LAPLACIAN ESTIMATION

STATEMENT AS TO FEDERALLY SPONSORED RESEARCH AND DEVELOPMENT

Embodiments of the present disclosure were developed with government support under award numbers 1622481 and 1914787 to Oleksandr Makeyev, awarded by the National Science Foundation (NSF) Division of Human Resource Development (HRD) Tribal Colleges and Universities Program (TCUP). The government has certain rights thereto.

BACKGROUND

Electroencephalography (EEG) is an essential tool for brain and behavioral research, as well as one of the mainstays of hospital diagnostic procedures and pre-surgical planning. Despite EEG's many advantages, the technology faces challenges such as poor spatial resolution, selectivity and low signal-to-noise ratio.

Noninvasive concentric ring electrodes (CREs) can resolve many of these problems. Noninvasive CREs have been shown to estimate the surface Laplacian, the second spatial derivative of the potentials on the scalp surface for the case of electroencephalogram, directly at each electrode instead of combining the data from an array of conventional, single pole, disc electrodes. Compared to EEG via disc electrodes, EEG via tripolar CREs has been demonstrated to have significantly better spatial selectivity, signal-to-noise ratio, and mutual information. CREs have found applications in a wide range of areas including brain-computer interfaces, epileptic seizure onset detection, detection of high-frequency oscillations, which may typically predict or precede seizures, and seizure onset zones, as well as in applications involving electroenterograms, electrocardiograms, and electrohysterograms. CREs could also be used for electrophysiological monitoring, e.g., during surgery.

BRIEF SUMMARY

Electrode devices and methods for electrophysiological measurement are provided. An electrode device may include an electrode substrate having a surface area. The electrode device may include a central disc electrode disposed on the electrode substrate and covering a central portion of the surface area. The central disc electrode may have a first radius, "R," of the central disc electrode relative to a center point of the central disc electrode. The electrode device may include a middle ring electrode concentric with the central disc electrode. The middle ring electrode may cover a first portion of the surface area of the electrode substrate between a second radius and a third radius from the center point. The second radius may be greater than the first radius. The electrode device may also include an outer ring electrode concentric with the central disc electrode and the middle ring electrode. The outer ring electrode may cover a second portion of the surface area of the electrode substrate between a fourth radius and a fifth radius from the center point. The fourth radius may be greater than the third radius and the fifth radius defining an active area of the electrode substrate. A first distance between the fourth radius and the fifth radius may be greater than at least one of a second distance between the second radius and the third radius or R.

In some embodiments, the central portion, the first portion, and the second portion together cover more than 50% of the active area of the electrode substrate. The first portion or the second portion may cover more than 25% of the active area of the electrode substrate. The second radius may be 2R, the third radius may be 3R, the fourth radius may be 4R, and the fifth radius may be 9R. The second distance may be greater than R. The middle ring electrode may be a first middle ring electrode, and the electrode device may include a second middle ring electrode concentric with the central disc electrode. The second middle ring electrode may be disposed on the electrode substrate covering a third portion of the surface area between a sixth radius and a seventh radius from the center point. The seventh radius may be smaller than the fourth radius and the sixth radius may be greater than the third radius. The first distance may be greater than a third distance between the sixth radius and the seventh radius. The first distance may be greater than the third distance and the third distance may be greater than the second distance. The third distance may be greater than the second distance and R. The second distance may be greater than R. The third distance may be greater than R.

Embodiments of the present disclosure may include an electrode device, including an electrode substrate having a surface area. The electrode device may include a central electrode disposed on the electrode substrate around a central portion of the surface area. The electrode device may also include a plurality of electrodes disposed on the electrode substrate concentric with the central electrode. The plurality of electrodes may include a first electrode covering a first portion of the surface area of the electrode substrate and a second electrode covering a second portion of the surface area of the electrode substrate. The second portion may be greater than a combined surface area of the first portion and the central portion.

In some embodiments, the surface area of the electrode substrate may extend to an outer periphery of the second electrode. The central portion and the plurality of electrodes together may cover more than 50% of the surface area of the electrode substrate. The surface area of the electrode substrate may extend to an outer periphery of the second electrode and the second portion may cover more than 25% of the surface area of the electrode substrate. The central electrode may be or include a disc covering a central region of the electrode substrate. A first distance between the first electrode and the second electrode may be greater than a distance between the central electrode and the first electrode. The electrode device may include a third electrode concentric with the central electrode and the first electrode. The third electrode may cover a third portion of the surface area of the electrode substrate and may be disposed on the electrode substrate between the first electrode and the second electrode.

Embodiments of the present disclosure may include a method of forming an electrode device. The method may include forming a central electrode on an electrode substrate. The central electrode may have a first radius, "R" relative to a center point of the central electrode. The method may include forming a middle electrode on the electrode substrate concentric with the central electrode. The middle electrode may be disposed on the electrode substrate between a second radius and a third radius from the center point. The second radius may be greater than the first radius. The method may also include forming an outer electrode on the electrode substrate concentric with the central electrode and the middle electrode. The outer electrode may be disposed on the electrode substrate between a fourth radius and a fifth radius from the center point. The fourth radius may be larger than the third radius. A first distance between the fourth radius and the fifth radius may be greater than at least one of a second distance between the second radius and the third radius or R.

In some embodiments, the middle electrode is a first middle electrode. The method may include forming a second middle electrode on the electrode substrate concentric with the central electrode. The second middle electrode may be disposed on the electrode substrate between a sixth radius and a seventh radius from the center point. The seventh radius may be smaller than the fourth radius. The method may include connecting the central electrode to a first terminal, connecting the middle electrode to a second terminal, and the outer electrode to a third terminal. The method may include connecting the second middle electrode to a fourth terminal. The outer electrode, the middle electrode, and the central electrode may include an electrode surface area covering more than 50% of an active area of the electrode substrate. The outer electrode may cover more than 25% of the active area of the electrode substrate. A distance between the middle electrode and the outer electrode may be greater than a distance between the central electrode and the middle electrode.

BRIEF DESCRIPTION OF THE DRAWINGS

FIG. 2A illustrates a face view of an example structure of a tripolar CRE, in accordance with some embodiments.

FIG. 2B illustrates a face view of an example structure of a tripolar CRE, in accordance with some embodiments.

FIG. 2C illustrates a face view of an example structure of a quadripolar CRE, in accordance with some embodiments.

FIG. 5 is a flow chart illustrating an example process for forming a CRE, in accordance with some embodiments.

DETAILED DESCRIPTION

Figure 1:
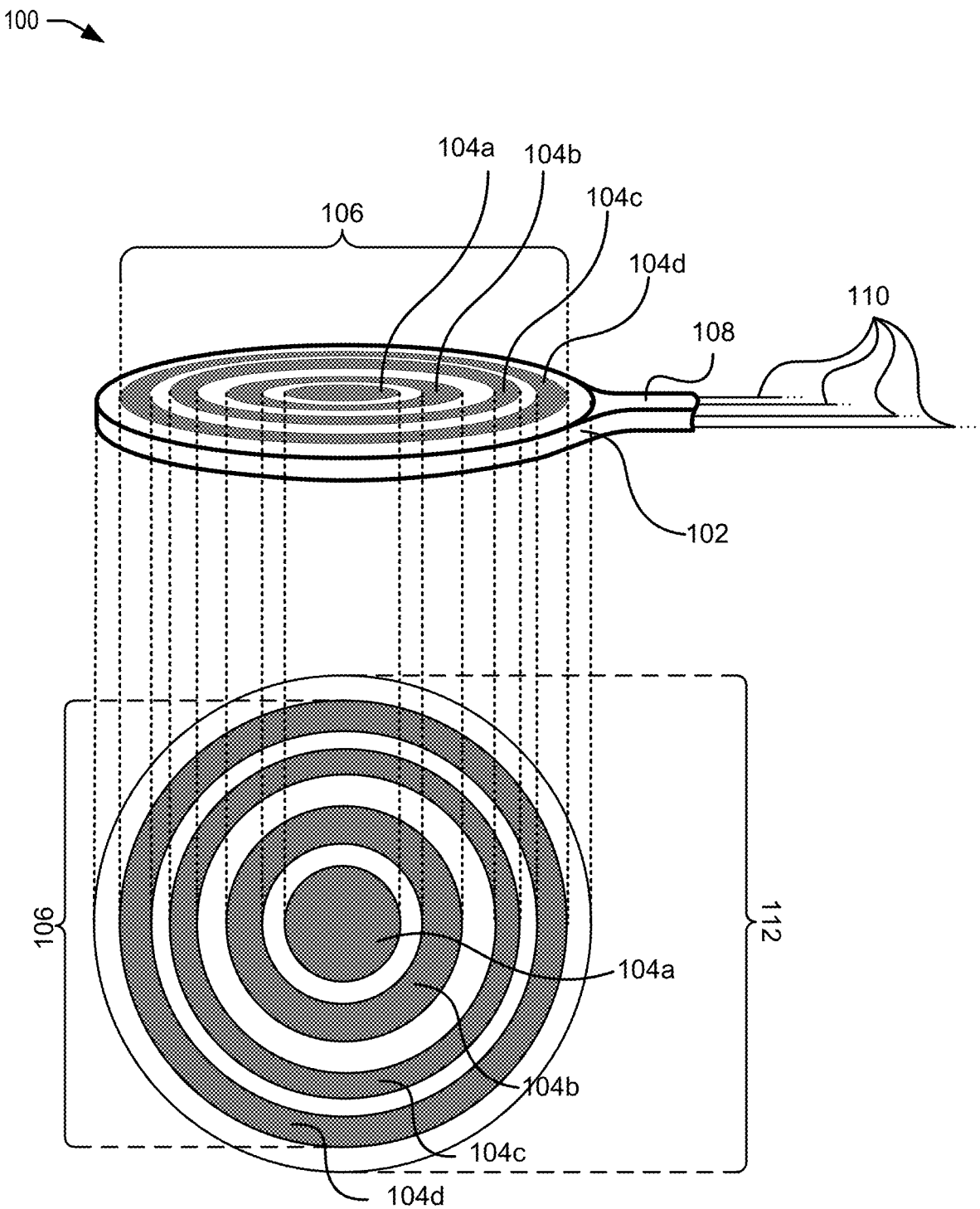
FIG. 1 illustrates a perspective view and a face view of an example a concentric ring electrode (CRE), in accordance with some embodiments.

Noninvasive concentric ring electrodes (CREs) can improve significantly on the performance of electroencephalography (EEG) systems. Noninvasive CREs can estimate the surface Laplacian, the second spatial derivative of the potentials on the scalp surface for EEG, directly at each electrode instead of combining the data from an array of conventional, single pole, disc electrodes. In particular, the disclosed electrode devices, systems, and methods can improve accuracy of electrophysiological measurement using CREs.

CREs may also be arranged in arrays in order to monitor and/or map the Laplacian at different locations. Compared to EEG via disc electrodes, EEG via CREs has significantly better spatial selectivity, signal-to-noise ratio, and mutual information. CREs have found applications in a wide range of areas including brain—computer interface, epileptic seizure onset detection, detection of high-frequency oscillations and seizure onset zones, as well as in applications involving electroenterograms, electrocardiograms (ECG), and electrohysterograms. CREs could also be used for electrophysiological monitoring, e.g. during surgery.

CRE systems have not made full use of variations in the CRE's geometrical configuration, such as the radii, spacing, and width of the ring electrodes. Moreover, existing estimates for the Laplacian from CRE measurements do not make optimal use of the information measured by the CRE.

The disclosed system and methods can improve over conventional systems by improving accuracy of the surface Laplacian estimation, in light of the primary biomedical significance of such measurements. In particular, electrode devices and methods of using such electrode devices may reduce Laplacian estimation error by as much as three-fold, relative to typical electrode devices used for electrophysiological measurement that incorporate concentric electrodes. Improved accuracy of Laplacian estimation, in turn, may provide improved health-outcomes including, but not limited to, spatial localization of diagnostic measurements, observation of patient physiological functioning, or techniques for prolonged measurements without implantation of electrodes.

In a particular example, a CRE may include multiple recording surfaces, such as a central disc electrode and a pair of concentric ring electrodes. The central disc electrode and the concentric ring electrodes may be disposed on an electrode substrate. The active area of the CRE may be defined as the area within which the central disc and the concentric rings are disposed. For example, in the case of concentric ring electrodes, the outer radius of the outermost concentric ring electrode may define the active area of the CRE. The electrodes may be coupled with leads and thereby connected to a signal receiving system. In some cases, the CRE may form a part of an array of CREs, positioned on a subject as part of measuring an electrophysiological signal. The electrodes may have differing widths, where the width may be defined by a difference between an outer radius and an inner radius of the electrodes in the case of circular ring electrodes. In the case of the central disc electrode, the width may be considered to be the radius, "R." Various configurations of the CRE include tripolar configurations, quadripolar configurations, pentapolar configurations, with various width profiles, and varying distances between each consecutive electrode, also referred to as an inter-electrode spacing.

Accordingly, the disclosed systems can improve over conventional systems and devices that measure electrostatic potentials by measuring these potentials more accurately through improved CRE electrode configurations. Such improvements can provide improved patient experiences including, but not limited to, shorter and/or less invasive procedures, as well as improved health outcomes such as improved diagnostic and preventive measures. Moreover, the disclosed systems, devices, and methods may provide cost savings and efficiency improvements, for example, by enabling more accurate readings with fewer recording sites and/or fewer electrodes. In particular, improved electrode configurations may provide cost improvements by obviating the need to upgrade or replace existing CRE equipment.

I. CONCENTRIC RING ELECTRODE CONFIGURATIONS

FIG. 1 illustrates a perspective view and face view of an example CRE 100, in accordance with some embodiments. The views presented in FIG. 1 provide an illustrative example of a CRE incorporating multiple electrodes that may be used for electrophysiological measurements with improved accuracy. The CRE 100 may form a part of a measurement system for diagnostic measurement of patient nerve function. The configuration and number of electrodes of the CRE 100 may provide significant improvements over state of the art electrodes, as described below. The CRE 100 includes an electrode substrate 102, upon which a number of recording surfaces is formed. The recording surfaces may be or may be defined at electrodes 104a-d, which are disposed within an active area 106 of the CRE 100. As shown, the active area 106 extends to the outer edge of an outermost electrode 104d, and as such covers less surface area than the entire surface 112 of the electrode substrate 102. In some examples, the surface area of the active area 106 may be coextensive with the entire surface 112 of the electrode substrate 102. The active area 106 is in-plane with the entire surface 112 of the electrode substrate 102. In some examples, however, the electrodes 104 may be formed having differing heights relative to the electrode substrate 102, may be flush with the electrode substrate 102, may be recessed into the electrode substrate 102, or may be proud of the electrode substrate 102.

The CRE 100 includes a contact 108 housing leads 110. In some examples the contact 108 may include, but is not limited to, a fixed connection to the leads 110 or a detachable connector facilitating removal of the electrode substrate 102 from the leads 110. The leads 110 may be individual connections or terminals electrically coupled to each of the electrodes 104 and configured to apply or measure a voltage as part of electrophysiological measurement. In some embodiments, the electrodes 104 and the leads 110 may be printed on a shared substrate 102, on different layers of a multilayer substrate 102, or formed internal to a composite substrate 102. The CRE 100 may be fabricated using circuit-printing techniques, lamination, additive manufacturing, or other approaches to form discrete recording surfaces (e.g., the electrodes 104) within the active area 106.

As illustrated, the electrodes 104 are formed as concentric rings. For example, a central electrode 104a may be formed on the electrode substrate 102, around which may be formed electrodes 104b-d, such as a first middle ring electrode 104b, a second middle ring electrode 104c and an outer ring electrode 104d. The configuration, shape, and number of the electrodes 104 of the CRE 100 provide improved performance for estimating the Laplacian of a voltage signal, which, in turn, improves the performance of the CRE 100 for electrophysiological measurements. For example, the central electrode 104a may be a disc, a ring, or another shape, such that it is symmetric about a central point of the active area 106.

As described in more detail in reference to FIGS. 2-3, below, the CRE 100 may include three electrodes 104 (a tripolar configuration), four electrodes 104 (a quadripolar configuration), five electrodes 104 (a pentapolar configuration), or more. In some embodiments, the size and position of the electrodes 104 are such that one or more general principles of CRE 100 configuration are satisfied. For example, the central electrode 104a and the concentric electrodes 104b-d may be formed such that an inter-electrode spacing between the electrodes 104 is minimized within the constraints of the physiological application, where the spacing may be described by a separation between the outer edges of adjacent electrodes 104 or by a distance between the electrodes 104 as measured from a center radius of adjacent electrodes 104. For example, salt bridging between the electrodes 104 caused by ions in or on a surface on which the CRE 100 is placed, such as the skin of a patient, may result in coupling between the electrodes 104. In this way, a minimum inter-electrode distance may be greater than or about 0.01 mm, greater than or about 0.1 mm, greater than or about 0.5 mm, greater than or about 1 mm, greater than or about 5 mm, or greater.

Similarly, the CRE 100 may include electrodes 104 having a minimum radius and minimum width, except for the outer ring electrode 104d. In the context of electrode dimensions, a minimum radius and minimum width may describe the dimensions forming a contact area for measuring electrophysiological signals. For example, the minimum radius may be related to the minimum spacing between the electrodes 104 and the minimum width of each of the electrodes 104 for which signal strength permits accurate measurement. Signal strength may describe a signal to noise ratio such that a periodic electrophysiological signal may be accurately measured (e.g., ECG, EEG signals, etc.). Similar to the discussion regarding minimum inter-electrode spacing, the dimensions of the electrodes 104 may depend at least in part on physiological characteristics of the subject as well as the type of measurement being performed. As such, different configurations of the CRE 100 may be better suited to some measurements than others, with the understanding that a larger active area 106 may include larger electrodes 104, and in turn may measure a stronger electrophysiological signal. Balancing this, however, is spatial resolution of measurements using the CRE, which tends to favor a smaller active area 106 in applications for measuring specific electrophysiological signals within a region having multiple periodic systems or within a space restriction (e.g., sensors for pediatric applications). In some embodiments, the active area 106 may be circular with a diameter greater than or about 5 mm, greater than or about 10 mm, greater than or about 20 mm, greater than or about 30 mm, greater than or about 40 mm, greater than or about 50 mm, greater than or about 60 mm, greater than or about 70 mm, greater than or about 80 mm, greater than or about 90 mm, greater than or about 100 mm, or greater. As described in more detail in reference to FIG. 3, rather than being described explicitly in terms of spatial dimensions, the dimensions of the electrodes 104 may be described in terms of fractional coverage of the active area 106 or in terms of multiples of a radius of the central electrode 104a.

In some embodiments, the electrodes 104 may have differing widths, which may provide improved performance. For example, increasing the width of an electrode 104 closer to the outer edge of the active area 106 may be advantageous to increasing the width of an electrode 104 closer to the central electrode 104a in the context of Laplacian estimation error. As an illustrative example, the central electrode 104a may be a disc of radius "R," the first middle ring electrode 104b, between an inner radius and an outer radius, may be wider than R, the second middle ring electrode 104c may be wider than the first middle ring electrode 104b, and the outer ring electrode 104d may be wider than the second middle ring electrode 104c. In some embodiments, one or more of the middle ring electrodes 104b-c may be wider than either the central electrode 104a or the outer ring electrode 104d.

In some embodiments, increasing the distance between the electrodes 104 closer to the outer edge of the active area 106 may provide improved electrophysiological measurement, relative to configurations with increasing distance between the electrodes 104 closer to the central electrode 104a. As described in more detail in reference to FIGS. 3A-3F, the electrodes 104 may be separated by a variable inter-electrode spacing. In some cases, the inter-electrode spacing may increase with each consecutive concentric electrode. For example, the outer ring electrode 104d may be spaced farther from the outer edge of the second middle ring electrode 104c than the inner edge of the second middle ring electrode 104c is spaced from the outer edge of the first middle ring electrode 104b. In some cases, the spacing may increase non-linearly according, for example, to a spacing function (e.g., a geometric function, a quadratic function, a cubic function, a sigmoidal function, an exponential function, etc.).

In some embodiments, the electrodes 104 account for a portion of the active area 106 greater than or about 45%, greater than or about 50%, greater than or about 55%, greater than or about 60%, greater than or about 65%, greater than or about 70%, greater than or about 75%, or greater, of the total active area 106. In some cases, the outer ring electrode 104d, the second middle ring electrode 104c, or the first middle ring electrode 104b may individually cover about 25% or more, about 30% or more, about 35% or more, about 40% or more, about 45% or more, about 50% or more, or a larger portion of the active area 106.

While the CRE 100 is illustrated as a quadripolar electrode, embodiments of the present disclosure also include other electrode configurations. In some embodiments, the alternative configurations may similarly be described by characteristics described in reference to the CRE 100. For example, the electrode configurations described in the following paragraphs may include fewer electrodes than the CRE 100 that may nonetheless cover more than 50% of the corresponding active area of the electrode substrate. Similarly, other CRE configurations may also include varying inter-electrode spacing, as described in more detail in reference to FIGS. 2A-2C and FIGS. 3A-3F, below.

FIG. 2A illustrates a face view of an example structure of a tripolar CRE 200, in accordance with some embodiments. The CRE 200 is an example of the CRE 100. The CRE 200 includes multiple recording surfaces, such as a central electrode 202, a middle ring electrode 204, and an outer ring electrode 206. In some embodiments, these recording surfaces may be composed of one or more metals or conductive materials, including but not limited to silver, gold, copper, tin, aluminum, silver chloride, or any other conductor. In some embodiments, the recording surfaces may also contain other materials, such as non-conducting materials. The recording surfaces may be separated by dielectrics, such as empty space or air, or any other dielectric or insulating material. In some embodiments, the CRE 200 may be removably affixed to, or contact, a patient's head or scalp, to perform EEG. In particular, the CRE 200 may measure the surface Laplacian, or the second spatial derivative, of the electrostatic potential on the patient's scalp surface. In various embodiments, CRE 200 may be used for brain-computer interfaces, epileptic seizure onset detection, detection of high-frequency oscillations, which may typically predict or precede seizures, and seizure onset zones, as well as in applications involving electroenterograms, ECG, electrohysterograms, or any other kind of electrophysiological monitoring, e.g. during surgery.

In some embodiments, the CRE 200 may be used to measure the electric potential at the recording surfaces, or an average of the potential over the areas of the respective recording surfaces. In some embodiments, the measured ring potentials may be relative to a reference potential such as the central disc potential, for example the respective potentials associated with the concentric electrodes 204 and 206 may be measured and/or expressed as differences from the potential of the central electrode 202. In turn, these potential measurements may be used to estimate a surface Laplacian, or second spatial derivative, given in polar coordinates for a radially symmetrical CRE configuration as $$\Delta v_0 \equiv \left( \frac{\partial^2}{\partial r^2} + \frac{1}{r}\frac{\partial}{\partial r} + \frac{1}{r^2}\frac{\partial^2}{\partial \theta^2} \right) v_0,$$

of the electric potential $v_0$, near the center of the CRE 200 or the central electrodes 202. The potentials or potential differences may also be referred to as voltages. Note that the spatial coordinates r and θ represent coordinates in the plane of the CRE 200. For example, if the CRE 200 is configured parallel to a patient's scalp in order to measure the surface Laplacian along the scalp, the rθ-plane may be parallel to the scalp.

FIG. 2B illustrates a face view of an example structure of a tripolar CRE 220, in accordance with some embodiments. The CRE 220 is an example of the CRE 200. In this example, the central electrode 222 is similar in radius as the central electrode 202 of the example of FIG. 2A, but the ring electrodes 224 and 226 vary in size relative to the ring electrodes 204 and 206 of FIG. 2A. As a result, the ratios of various geometrical features of CRE 220 differ from those of CRE 200 in FIG. 2A. For example, the thickness of the outer ring electrode 226 is greater for CRE 220 than for CRE 200. Similarly, in this example, the inter-electrode separations may be considered to vary for CRE 220 because the radial separation from ring electrode 224 to the outer periphery of central electrode 222 may be greater than the radial separation between ring electrode 226 and ring electrode 224. By contrast, CRE 200 in the example of FIG. 2A may have constant inter-electrode spacing. The inter-electrode spacing may also be referred to herein as inter-electrode distances or intervals.

In some embodiments, the disclosed system and methods may make use of such geometrical or other variations to provide improved accuracy and precision of physiological measurements. For example, the ring radii, width, or inter-electrode spacings may affect the measurement performance, sensitivity, and/or accuracy of the CRE. Electrode configurations may also improve the accuracy of measurement of the surface Laplacian. Such improvements may lead to improved patient experiences such as shorter procedures, as well as to improved health outcomes. Moreover, the disclosed system may provide cost savings, for example, by enabling accurate readings with less equipment.

Other variations are also possible, such as: geometrical variations (e.g., using non-concentric or non-circular rings, or otherwise varying the sizes, separations, number, or shapes of recording surfaces); material or composition variations (e.g., using different metals or alloys for the recording surfaces, varying the materials of different recording surfaces within a single CRE, etc.); or other variations, and are not limited by the present disclosure. Electrode configurations described herein may improve estimation of a potential Laplacian, and/or optimize other aspects of methods for estimating the Laplacian, or other electrical characteristics measured by the CRE, as described herein below.

FIG. 2C illustrates a face view of an example structure of a quadripolar CRE 240 with three concentric electrodes, in accordance with some embodiments. The CRE 240 is an example of the CRE 200. In this example, a central disc electrode 242 serves as the central electrode. While FIGS. 2A-2C illustrate examples of CREs having a central disc electrode, some embodiments include a central electrode that is not circular. For example, the central electrode may be polygonal, or may be oblong, such that it is centered and symmetric about a source location for an electrophysiological signal. The central disc electrode 242, and two inner ring electrodes 244 and 246 of CRE 240 have similar sizes, shapes, and separations compared with the central disc 202 and rings 204 and 206 of CRE 200 in the example of FIG. 2A. However, CRE 240 also includes an additional ring electrode 248, for a total of three ring electrodes, or four recording surfaces including the central disc electrode 242.

In some examples, CREs with additional recording surfaces, such as additional ring electrode 248, may have improved measurement performance, sensitivity, and/or accuracy. In an example, an estimate of the surface Laplacian of the electrostatic potential near the central disc electrode 242 or the center of the CRE may improve systematically as the number of concentric electrodes is increased. In some embodiments, the CRE can have any number of concentric electrodes, and is not limited by the present disclosure. However, in order to make optimal use of the additional recording surfaces, the system may combine the measured potentials based on a formula and/or coefficients that are optimized for the particular geometry of the CRE. Thus, in general, the formula and/or set of coefficients may depend on the number n of concentric electrodes.

For example, the system may make use of a different set of coefficients for a CRE with n rings than it does for a CRE with a different number m of rings. For example, coefficients associated with the inner ring electrodes 244 and 246 of quadripolar CRE 240 may differ from the respective coefficients associated with electrodes 204 and 206 of the tripolar CRE 200 of FIG. 2A. Of course, the system can also use a coefficient associated with outermost ring electrode 248 of quadripolar CRE 240, which has no counterpart ring in tripolar CRE 200. Moreover, in some embodiments, such a coefficient associated with outermost ring 248 may also differ from the coefficient associated with outer ring electrode 206 of the tripolar CRE 200, even though the outer ring electrode 206 is the outermost concentric electrode of CRE 200.

Figure 3A:
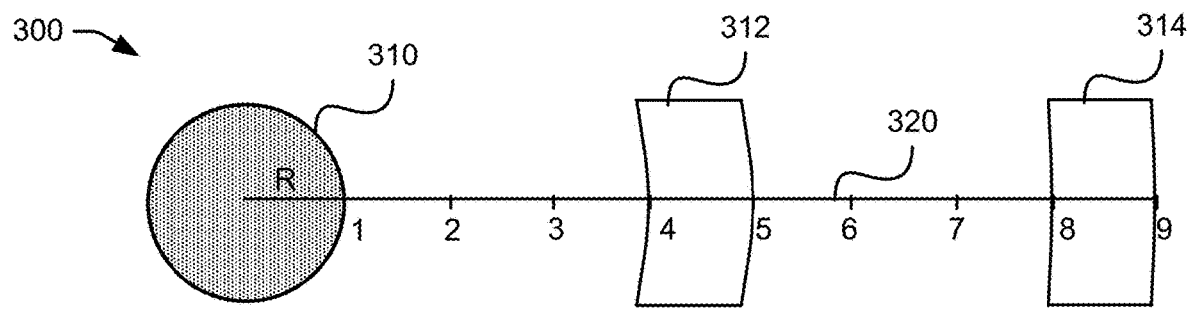
FIG. 3A illustrates a diagrammatic view of an example tripolar CRE, in accordance with some embodiments.

FIG. 3A illustrates a diagrammatic view of an example tripolar CRE 300, in accordance with some embodiments. As described in reference to FIGS. 1-2B, above, the tripolar CRE 300 includes a central electrode 310 having a radius, "R," a first electrode 312, and a second electrode 314. The first electrode 312 and second electrode 314 are illustrated as sections for simplicity of explanation, but describe electrodes centered concentrically around the central electrode 310. A de-dimensionalized coordinate system 320, defined in reference to the radius R of the central electrode 310 is provided to permit the direct comparison of multiple different CRE configurations, without regard to overall size of the CREs that may differ for different applications. For simplicity in comparison, each example CRE configuration presented in FIG. 3A-3F are described with the same de-dimensionalized coordinate system 320, although it is understood that other relative dimensions are contemplated for different CRE configurations. In FIG. 3A, the tripolar CRE 300 includes constant inter-electrode spacing, with the first electrode 312 covering between approximately 4R-5R, and the second electrode 314 covering between approximately 8R-9R. The CRE configuration illustrated in FIG. 3A corresponds to a constant-distance arrangement, which may result in higher error when estimating the Laplacian of surface potentials. The CRE configuration of FIG. 3A is but one example embodiment, where many other possible configurations are contemplated herein.

Alternative tripolar CRE configurations may include, but are not limited to, those described in Table 1, below. For integer values of each parameter, a tripolar CRE with an outer radius of 9R may have 70 different configurations, of which 12 are summarized in Table 1. In some embodiments, some configurations provide improved estimation error relative to other configurations. For example, in Table 1, CRE configuration number 6 may be characterized by an error as much as 100% higher than configuration number 1, while configuration number 2 may be characterized by an error only as much as 1% higher than configuration number 1. In this way, configurations that conform to the principles described in reference to FIG. 1 may provide improved Laplacian estimation, and thus may improve overall performance for electrophysiological measurements.

TABLE 1

| Config- uration Number | Central Electrode 310 Radius, R | First Electrode 312 | | Second Electrode 314 | |
|---|---|---|---|---|---|
| | | Inner Radius | Outer Radius | Inner Radius | Outer Radius |
| 1 | 1 | 2 | 3 | 4 | 9 |
| 2 | 1 | 2 | 3 | 5 | 9 |
| 3 | 1 | 2 | 3 | 6 | 9 |
| 4 | 1 | 2 | 3 | 7 | 9 |
| 5 | 1 | 2 | 3 | 8 | 9 |
| 6 | 1 | 3 | 4 | 8 | 9 |
| 7 | 1 | 4 | 5 | 8 | 9 |
| 8 | 4 | 5 | 7 | 8 | 9 |
| 9 | 2 | 6 | 7 | 8 | 9 |
| 10 | 3 | 6 | 7 | 8 | 9 |
| 11 | 4 | 6 | 7 | 8 | 9 |
| 12 | 5 | 6 | 7 | 8 | 9 |

Figure 3B:
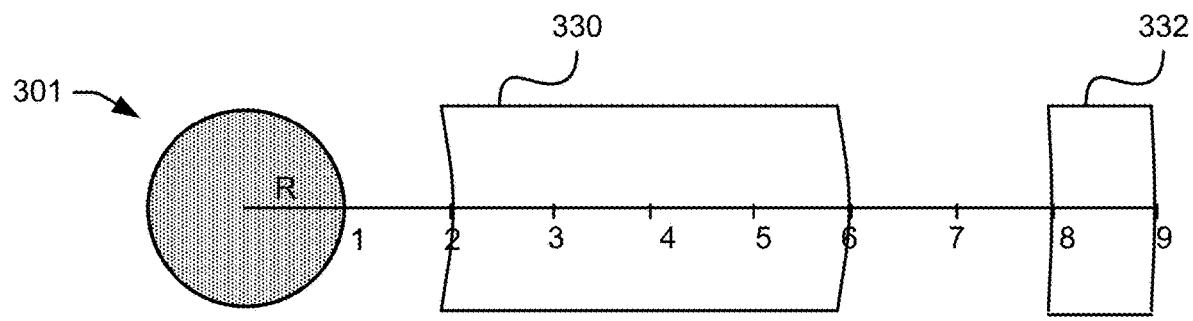
FIG. 3B illustrates a diagrammatic view of an example tripolar CRE, in accordance with some embodiments.

FIG. 3B illustrates a diagrammatic view of an example tripolar CRE 301, in accordance with some embodiments. In contrast to the CRE configurations described in reference to FIG. 3A, CRE 301 includes a relatively wide first electrode 330 and a relatively narrow second electrode 332. In the tripolar CRE 301, the first electrode 330 is positioned to cover between 2R-6R, while the second electrode 332 is positioned to cover between 8R-9R. As such, the first electrode 330 may cover as much as 30% or more, as much as 40% or more, 50% or more, 60% or more, or more of the active area of the CRE, $81\pi R^2$, that is bounded by the outer radius of the second electrode 332.

Figure 3C:
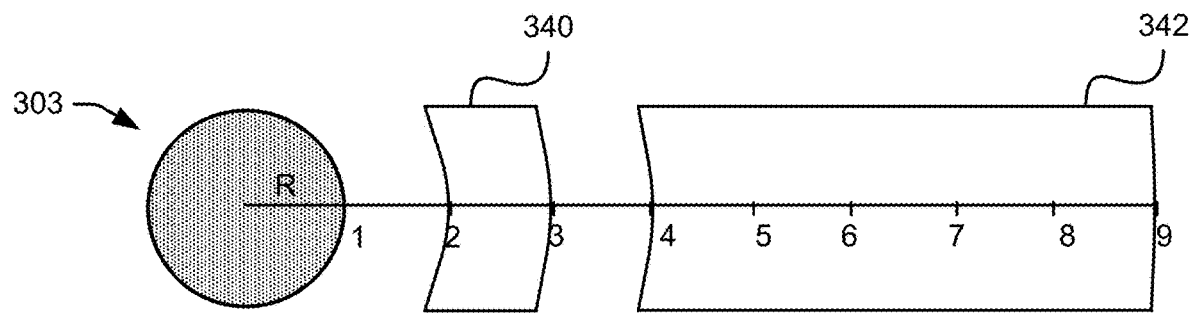
FIG. 3C illustrates a diagrammatic view of an example tripolar CRE, in accordance with some embodiments.

FIG. 3C illustrates a diagrammatic view of an example tripolar CRE 303, in accordance with some embodiments. Similar to the tripolar configuration described in reference to FIG. 3B, the tripolar CRE 303 includes a relatively narrow first electrode 340 and a relatively wide second electrode 342. In such configurations, the second electrode 342 may cover as much as 20% or more, 25% or more, 30% or more, 40% or more, 50% or more, 60% or more, or more of the active area of the CRE 303. For example, as illustrated, the first electrode 340 covers between 2R-3R and the second electrode 342 covers between 4R-9R. As such, the second electrode 342 covers as much as 90% of the active area of the CRE 303. While the CRE 303 includes constant inter-electrode spacing, tripolar CREs are not limited to integer R values of inter electrode spacing. For example, a CRE may include an inter-electrode spacing of between 0-R, between R-2R, between 2R-3R, or larger, depending on the extent of the active area (e.g., where the radius of the active area is larger than 9R).

Figure 3D:
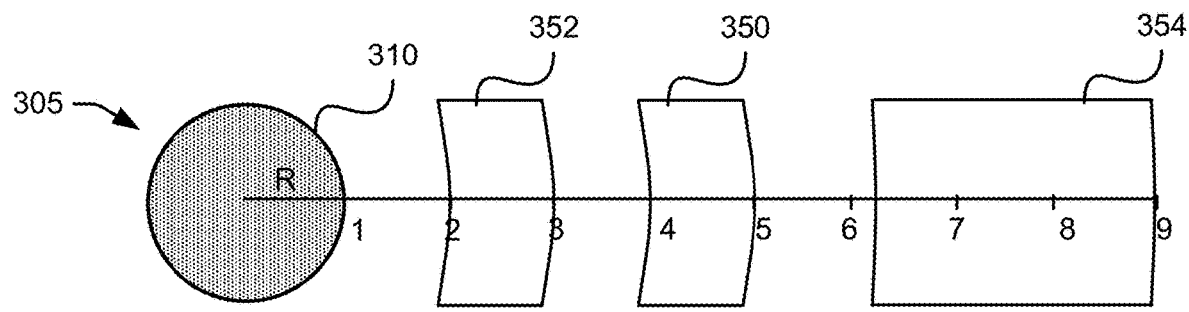
FIG. 3D illustrates a diagrammatic view of an example quadripolar CRE, in accordance with some embodiments.

FIG. 3D illustrates a diagrammatic view of an example quadripolar CRE 305, in accordance with some embodiments. As described in reference to FIG. 1, above, and FIG. 2C, above, the quadripolar CRE 305 may include a third electrode 350, positioned between a first electrode 352 and a second electrode 354 of a tripolar configuration. Quadripolar CREs may provide improved Laplacian estimation relative to tripolar CREs, since Laplacian estimation error corresponds to truncation error of a Taylor series expansion. Additional ring electrodes (e.g., quadripolar as opposed to tripolar or bipolar configurations) permit additional truncation terms to be cancelled, which in turn decreases the truncation error. As shown, similar variation in electrode width and spacing may be included in quadripolar CRE configurations as seen in tripolar CRE configurations. For example, the first electrode 352 of CRE 305 covers between 2R-3R on the active area, the third electrode 350 covers between 4R-5R on the active area, and the second electrode 354 covers between 6.2R-9R of the active area, where the active area is bounded by the outer radius of the second electrode 354, 9R. As illustrated in FIG. 3D, the second electrode 354 has a non-integer width. In the configuration shown, the second electrode 354 covers approximately 53% of the active area ($81\pi R^2$). In some embodiments, the second electrode 354, the first electrode 352, or the third electrode 350 may cover as much as 25% or more, 30% or more, 35% or more, 40% or more, 50% or more, 55% or more, or a larger portion of the active area of the quadripolar CRE 305.

Figure 3E:
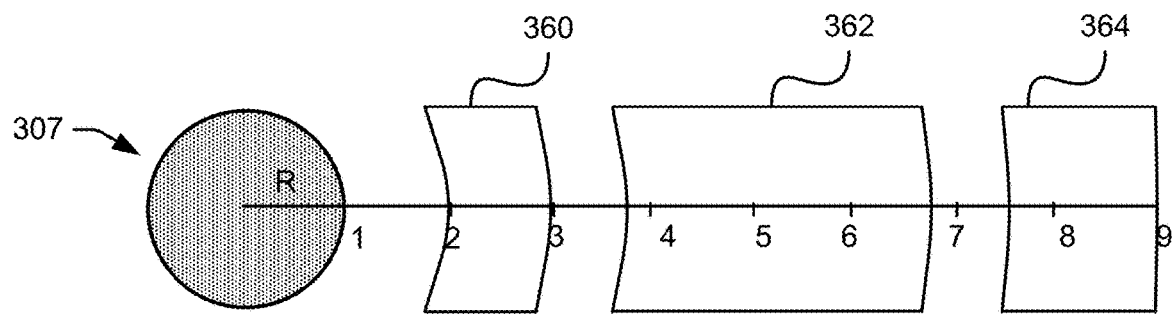
FIG. 3E illustrates a diagrammatic view of an example quadripolar CRE, in accordance with some embodiments.

FIG. 3E illustrates a diagrammatic view of an example quadripolar concentric ring electrode 307, in accordance with some embodiments. As an illustrative example of another quadripolar CRE having a relatively wide third electrode 362, the CRE 307 includes a third electrode 362 covering between 3.8R-6.8R, a second electrode 364 covering between 7.5R-9R, and a first electrode 360 covering between 2R-3R. In this exemplary configuration, the third electrode 362 covers approximately 40% of the active area of the CRE 307, while total coverage of the recording surfaces, made up of all three electrodes and the central electrode 310, is approximately 76% of the active area of the quadripolar CRE 307 ($81\pi R^2$) bounded by the outer radius of the second electrode 364.

Figure 3F:
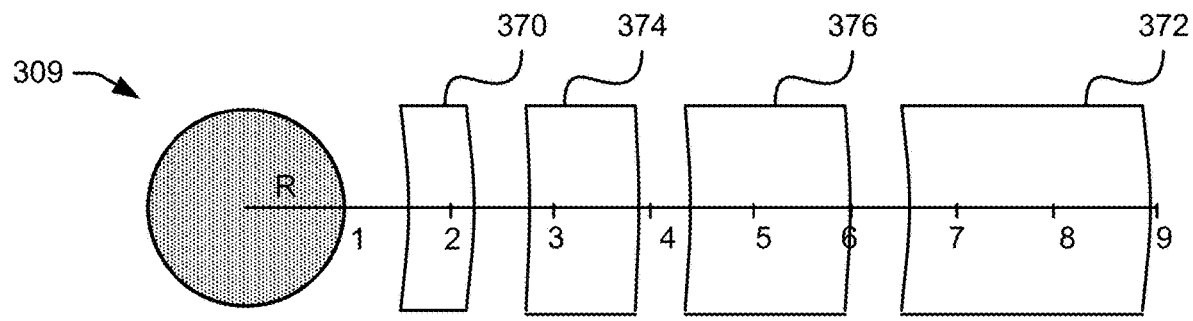
FIG. 3F illustrates a diagrammatic view of an example pentapolar CRE, in accordance with some embodiments.

FIG. 3F illustrates a diagrammatic view of an example pentapolar CRE 309, in accordance with some embodiments. Not being limited only to tripolar CREs and quadripolar CREs, embodiments of the present disclosure include CRE configurations including additional electrodes including four concentric electrodes, five concentric electrodes, six concentric electrodes, or more. As illustrated in FIG. 3F, the pentapolar CRE 309 includes a first electrode 370, a second electrode 372, a third electrode 374, and a fourth electrode 376, each concentric with the central electrode 310. The third electrode 374 and fourth electrode 376, in keeping with the numbering convention used for tripolar CREs, may be disposed on an electrode substrate (e.g., electrode substrate 102 of FIG. 1) between the first electrode 370 and the second electrode 372. In pentapolar configurations, as with configurations including fewer electrodes, each electrode may have a different width. As illustrated, the electrodes may progressively increase in width with increasing distance from the central electrode 310. For example, in the CRE 309 the first electrode 370 has a width less than R, the third electrode 374 has a width slightly greater than R, the fourth electrode 376 has a width slightly less than 2R, and the second electrode 372 has a width larger than 2R. In this example, the recording surfaces cover as much as 82% of the active area of the CRE ($81\pi R^2$). By providing concentric electrodes with different widths, however, the recording surfaces may cover portions of the active area exceeding 30% or more, 40% or more, 50% or more, 55% or more, 65% or more, 70% or more, 75% or more, 80% or more, 85% or more, or larger.

While the preceding descriptions focus on CRE configurations for which the active area of the CRE is $81\pi R^2$, corresponding to an outer radius of 9R, embodiments of the present disclosure include CREs with differing numbers of concentric electrodes, for which the outer radius of the active area may be larger than 9R or less than 9R, in integer multiples or non-integer multiples of R. Descriptions using R as a referential dimension are provided for simplicity of description and to generalize the application of the configurations described herein to multiple scales where the outer radius of the CRE is as much as 1 mm or larger, 1 cm or larger, or 10 cm or larger. In some embodiments, therefore, R may correspond to 1.1 mm for a CRE having an outer radius of 10 mm divided into nine intervals of R. As another example, for a CRE having an outer radius of 1.5 cm, divided into 100 intervals of R, R will correspond to a length of 0.15 mm.

II. ESTIMATING LAPLACIAN VIA FINITE DIMENSIONS MODEL (FDM)

In some embodiments, the Laplacian of a CRE may be estimated for the electrode configurations described in reference to FIG. 1, FIGS. 2A-C, and FIGS. 3A-F. The Laplacian may be described as the spatial derivative $$\Delta v_0 \equiv \left( \frac{\partial^2}{\partial x^2} + \frac{\partial^2}{\partial y^2} \right) v_0$$

or $$\Delta v_0 \equiv \left( \frac{\partial^2}{\partial r^2} + \frac{1}{r}\frac{\partial}{\partial r} + \frac{1}{r^2}\frac{\partial^2}{\partial \theta^2} \right) v_0,$$

(also denoted as $\nabla^2 v_0$) of the electrostatic potential $v_0$ near the center of a (n+1)-polar CRE with n concentric electrodes. In some embodiments, the system may apply a finite dimensions model (FDM), which considers multiple electrode parameters including, but not limited to, the radius of the central electrode 310 and the individual widths of concentric electrodes, to estimate the Laplacian. The FDM may treat the central electrode and concentric rings of the CRE as solid conductors to improve Laplacian error estimation over alternative methods, such as the negligible dimensions model. As illustrated in FIGS. 3A-F, CREs may include, but are not limited to, linearly increasing inter-ring distances, constant inter-ring distances configurations, linearly decreasing inter-ring distances, or configurations incorporating a non-linear separation progression. The FDM may describe electrode configurations in terms of a single CRE radius subdivided into a number of equal intervals, such as nine equal intervals. The central electrode and each concentric ring electrode may thus be described by an inner radius and an outer radius in reference to the radius "R," while the total active area of the CRE may be described as $81\pi R^2$. As one potential approach, an average potential on each electrode may be calculated using Huiskamp's Laplacian potential derivation based on the Taylor series expansion.

In some embodiments, this Laplacian estimate signal may be calculated using a custom preamplifier board, and may be sent to the clinical amplifier for each CRE. Alternatively, the Laplacian estimate may be calculated via a special- or general-purpose circuit or computer, a software module, or any other device, and is not limited by the present disclosure.

III. SYSTEM

Figure 4A:
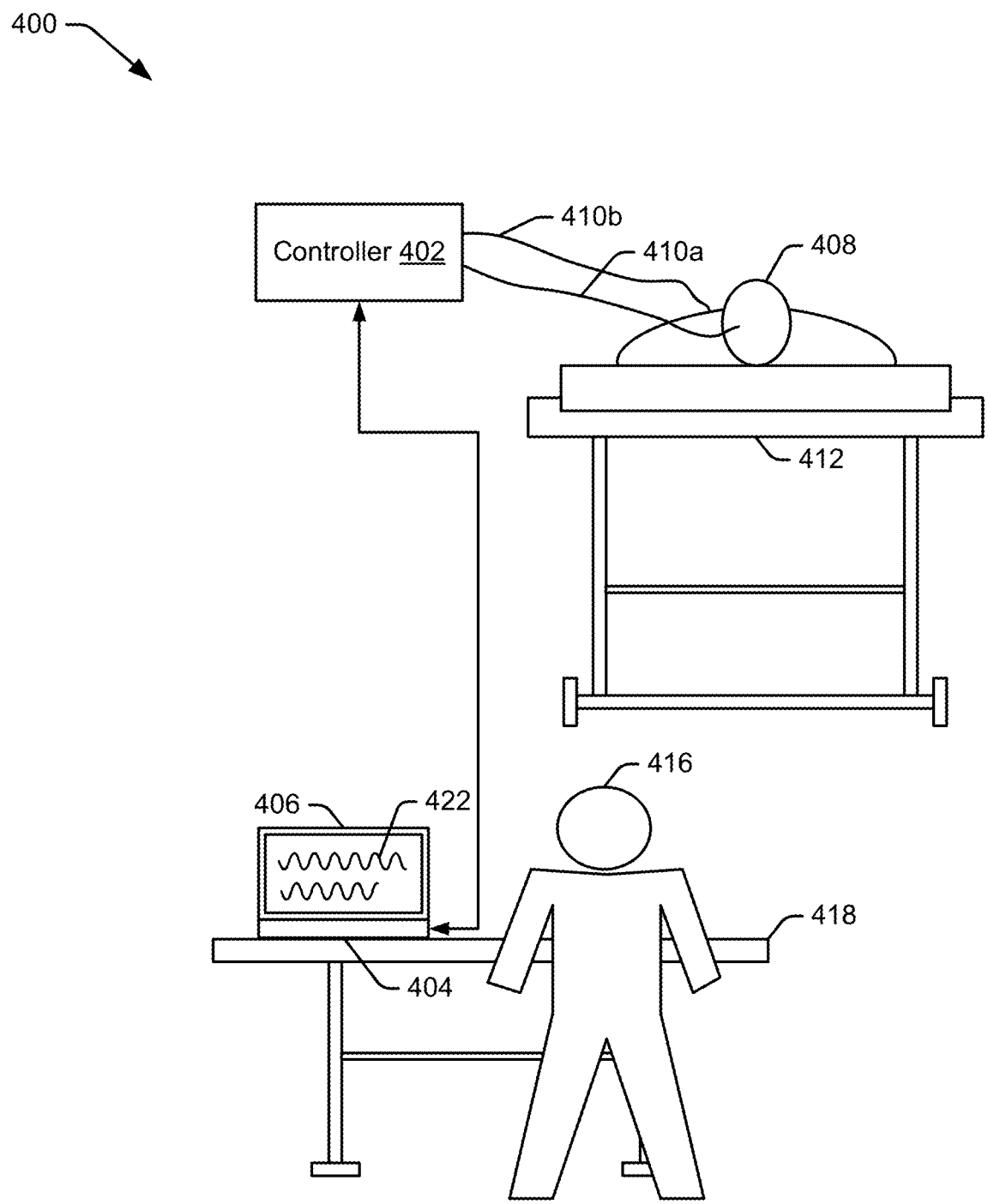
FIG. 4A illustrates an example neurophysiological monitoring system, in accordance with some embodiments.

FIG. 4A illustrates an example neurophysiological monitoring system 400, according to at least one example. The neurophysiological monitoring system 400 includes a monitoring system including a controller 402 and a computing device 404, and a display system including a display device 406. The controller 402 and the display device 406 may be electronically connected to the computing device 404 in any suitable manner (e.g., network cables, wireless networks, optical cables, power cables, input/output interfaces, etc.).

Generally, the computing device 404, which may be any suitable computing device, is configured to manage the operation of the controller 402 and generate and provide information for presentation at the display device 406. The controller 402, operating under at least partial control of the computing device 404, may be configured to generate, deliver, detect, and/or process electrical signals with respect to a patient 408, such as a patient undergoing EEG, brain-computer interfaces, seizure onset detection, detection of high-frequency oscillations and seizure onset zones, as well as in applications involving electroenterograms, electrocardiograms (ECG), electrohysterograms, or any other kind of electrophysiological monitoring. In particular, a CRE may measure the surface Laplacian, or the second spatial derivative, of the electrostatic potential on the patient's scalp surface. Thus, the controller 402 may be an example of a multimodal machine for simultaneous signal generation, detection, and recording. Such signals may be referred to as neurological data or electrophysiological data. In some examples, the controller 402 may receive commands from the computing device 404 to send electrical signals to the patient 408. Response signals may be detected or generated by the patient 408 in response to electrical signals from the controller 402. These response signals are passed by the controller 402, which may perform some filtering and/or processing, to the computing device 404. The computing device 404, executing monitoring modules (e.g., dedicated hardware, firmware, or software), may be configured to receive, augment, and/or otherwise process the response signals prior to providing representations of the response signals for presentation at the display devices 406. The modules of the computing device 404 may allow simultaneous viewing of multiple tests. In some examples, the tests are viewed on the display device 406.

The system may monitor and/or stimulate the patient 408, e.g. for seizure detection and/or control or brain-computer interface, via one or more electrodes 410a, 410b, such as a CRE (e.g., CRE 100 of FIG. 1). The monitoring may occur as electrical signals that are introduced at the second electrode 410b and then detected by the first electrode 410a. In some embodiments, a plurality of CREs may also be arranged in arrays, such as regular arrays, in order to monitor and/or map out the Laplacian of the potential at different locations on or near a patient. Note that, using coefficients and/or a formula as disclosed herein, an individual CRE or each respective CRE in an array may measure the Laplacian directly, thereby reducing the computational burden for system 400 and/or a separate computer to compute the Laplacian. In some embodiments, such an array may be rectangular. In some embodiments, the disclosed system can also interpolate between the individual CREs in an array, in order to obtain a more detailed map of the potential and/or the Laplacian.

In some examples, the patient 408 may be situated on an operating table 412. The operating table 412 may be fixed or mobile, and may include adjustability. In some examples, the operating table 412 may include grounding connections, adapters for supporting the electrodes 410 and/or components of the controller 402.

In some embodiments, the display device 406 may be positioned away from the patient 408. For example, the display device 406 may be supported by a table 418. The display device 406 may be electronically and/or physically connected to the computing device 404. For example, the computing device 404 may be a laptop and the display device 406 may be a monitor of the laptop.

In some examples, the positioning of the display device 406 may be relative to a user 416 such as a clinically trained and certified technologist. For example, the display device 406 may be positioned such that a display surface of the display device 406 is viewable (e.g., within a field of view) by the user 416.

Figure 4B:
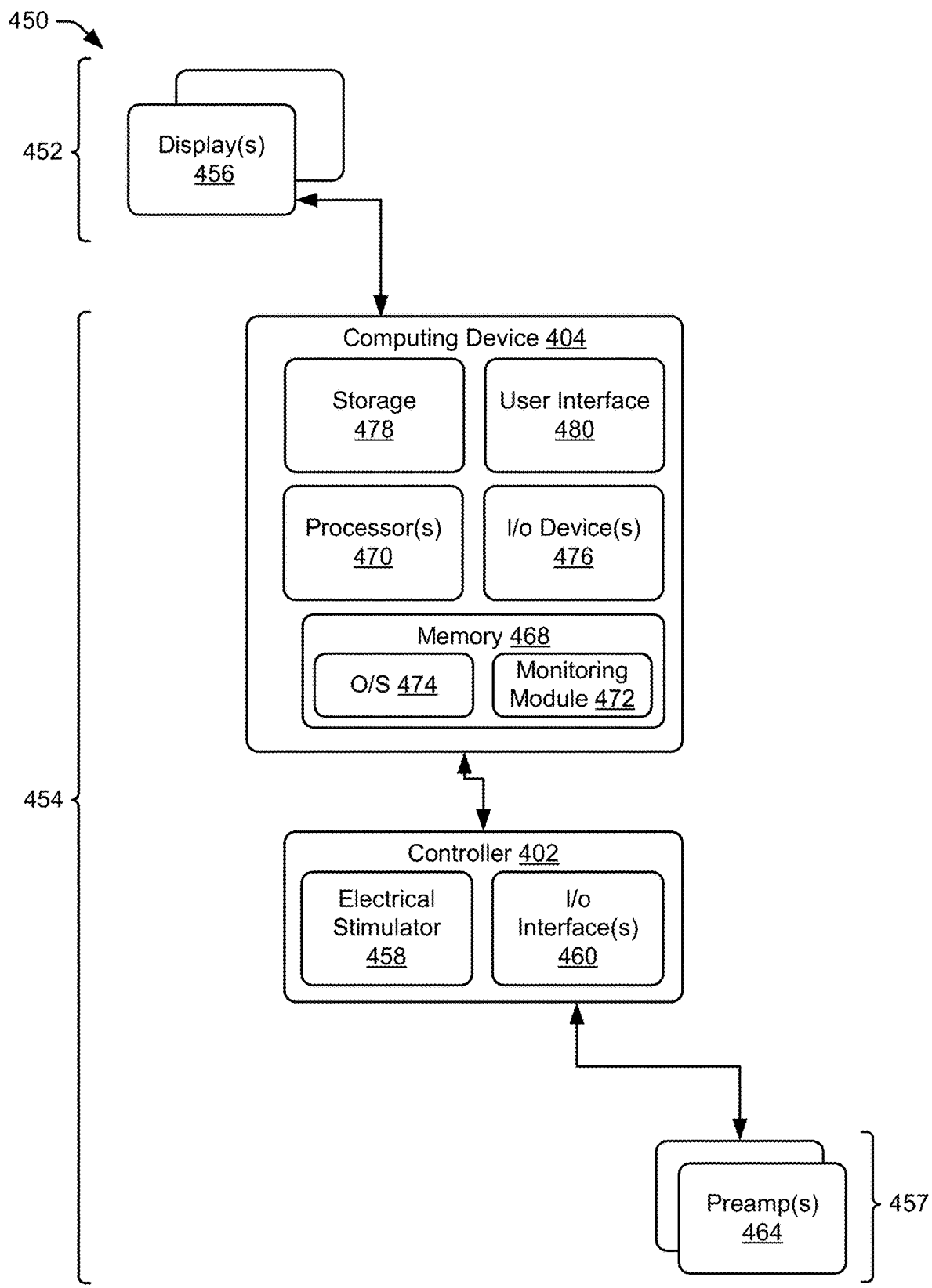
FIG. 4B illustrates components of an example neurophysiological monitoring system, in accordance with some embodiments.

FIG. 4B illustrates components of an example neurophysiological monitoring system 450, according at least one example. The neurophysiological monitoring system 450 is an example of the neurophysiological monitoring system 400 described herein. Thus, the neurophysiological monitoring system 450 includes a display system 452 and a monitoring system 454. Like the display system described with reference to FIG. 4A, the display system 452 includes one or more display devices such as display devices 456. Like the display devices 406, the display devices 456 may be any suitable device capable of visually presenting information. Examples of such devices may include cathode ray tube (CRT) displays, light-emitting diode (LED) displays, electroluminescent displays (ELD), electronic paper, plasma display panels (PDP), liquid crystal displays (LCD), organic light-emitting diode (OLED) displays, surface-conduction electron-emitter displays (SED), field emission displays (FED), projectors (LCD, CRT, digital light processing (DLP), liquid crystal on silicon (LCoS), LED, hybrid LED, laser diode), and any other suitable device capable of displaying information. The display devices 456 may be positioned adjacent to the users 416.

The monitoring system 454 is an example of the monitoring system described with reference to FIG. 4A. To this end, the monitoring system 454 may include the computing device 404, the controller 402, and one or more attachment devices 457. The attachment devices 457 may be connected to the controller 402 in order to augment or otherwise enable certain functions of the controller 402. In some examples, the attachment devices 457 are themselves separate modules that are disposed between the controller 402 and the patient 408. The function of the example attachment devices 457 will be discussed later. Though a few examples of attachment devices 457 are illustrated, other and different attachment devices 457 may also be connected to the controller 402.

In various embodiments, either the controller 402 or the computing device 404 may store the linear combination coefficients for the potentials measured by the CRE. For example, an amplifier or preamplifier 464 included in or associated with controller 402 may be configured to calculate a Laplacian estimate from the potentials based on the coefficients. In some embodiments, the system 400 (such as controller 402 or computing device 404) may receive and store the coefficients.

In some embodiments, the controller 402 may include an electrical stimulator 458 and one or more input/output interfaces 460. The electrical stimulator 458 may include a wide variety of triggering modes and pulse outputs to provide electrical stimulation for a patient's nervous system. In some examples, the system may instead measure, detect, and/or image a patient or a target signal, such as an EEG signal, without stimulating the patient or target.

The attachment devices 457 also include one or more preamplifiers 464. The preamplifiers 464 are examples of digital preamplifier modules. In some examples, the preamplifiers 464 provide signal detection, amplification, montage selection, A/D conversion, antialiasing filtering, and digital signal processing. The preamplifiers 464 may route detected signals to the controller 402 via any suitable connection. Each preamplifier 464 may include inputs for the electrodes 410, such as a CRE and/or the recording sites of a CRE. The preamplifiers 464 may calculate a Laplacian estimate signal based on linear combination coefficients computed as disclosed herein.

The computing device 404 may be in communication with the other components of the neurophysiological monitoring system 450 via one or more network(s), wired connections, and the like. The network may include any one or a combination of many different types of networks, such as cable networks, the Internet, wireless networks, cellular networks, radio networks, and other private and/or public networks.

Turning now to the details of the computing device 404, the computing device 404 may include at least one memory 468 and one or more processing units (or processor(s)) 470. The processor(s) 470 may be implemented as appropriate in hardware, computer-executable instructions, software, firmware, or combinations thereof. For example, the processors 470 may include one or more general purpose computers, dedicated microprocessors, or other processing devices capable of communicating electronic information. Examples of the processors 470 include one or more application-specific integrated circuits (ASICs), field programmable gate arrays (FPGAs), digital signal processors (DSPs) and any other suitable specific or general purpose processors.

Computer-executable instruction, software, or firmware implementations of the processor(s) 470 may include computer-executable or machine-executable instructions written in any suitable programming language to perform the various functions described. The memory 468 may include more than one memory and may be distributed throughout the computing device 404. The memory 468 may store program instructions (e.g., a monitoring module 472) that are loadable and executable on the processor(s) 470, as well as data generated during the execution of these programs. Depending on the configuration and type of memory including the monitoring module 472, the memory 468 may be volatile (such as random access memory (RAM)) and/or non-volatile (such as read-only memory (ROM), flash memory, or other memory). In some embodiments, the monitoring module 472 may receive and/or adjust the linear combination coefficients for Laplacian estimation based on the potentials measured by the CRE. In some embodiments, monitoring module 472 may implement the linear combination based on these coefficients. The computing device 404 may also include additional removable storage 478 and/or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 468 may include multiple different types of memory, such as static random access memory (SRAM), dynamic random access memory (DRAM), or ROM. The memory 468 may also include an operating system 474.

The memory 468 and the additional storage 478, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the monitoring module 472. The modules of the monitoring module 472 may include one or more components, modules, and the like. For example, monitoring module 472 may include modules or components that receive, adjust, and/or implement the linear combination coefficients for Laplacian estimation based on the potentials measured by the CRE. The computing device 404 may also include input/output ("I/O") device(s) and/or ports 476, such as for enabling connection with a keyboard, a mouse, a pen, a voice input device, a touch input device, a display, speakers, a printer, or other I/O device. The I/O device(s) 476 may enable communication with the other systems of the neurophysiological monitoring system 450.

The computing device 404 may include a user interface 480. The user interface 480 may be utilized by an operator or other authorized user such as the user 416 to access portions of the computing device 404 (e.g., the monitoring module 472). In some examples, the user interface 480 may include a graphical user interface, web-based applications, programmatic interfaces such as application programming interfaces (APIs), or other user interface configurations.

IV. PROCESSES

Figure 6:
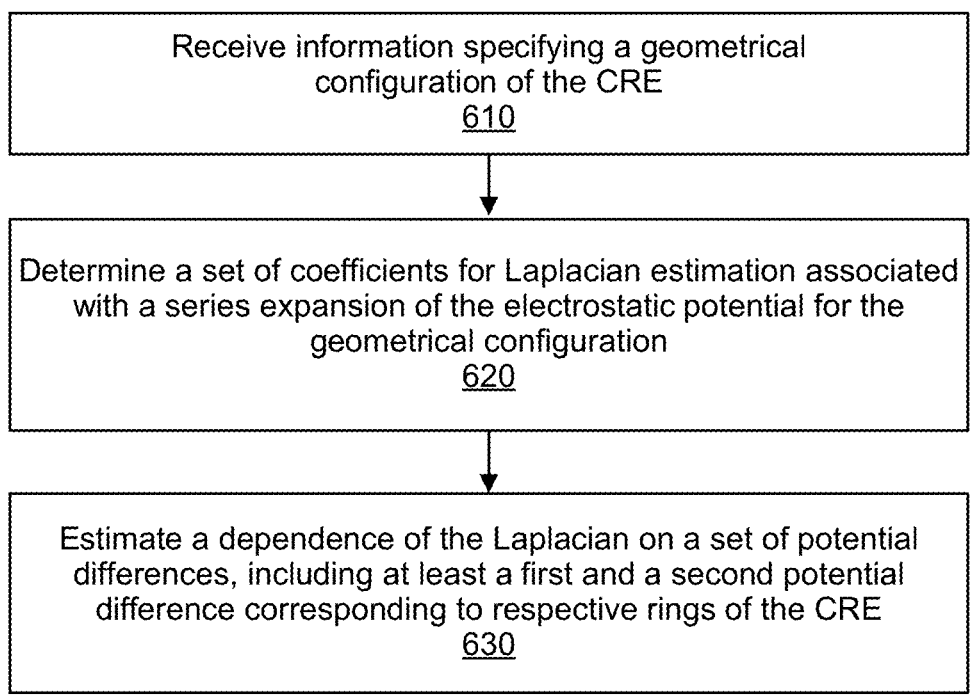
FIG. 6 is a flow chart illustrating an example process for determining a functional of an electrostatic potential measurable by a CRE, in accordance with some embodiments.

FIGS. 5 and 6 illustrate example flow diagrams showing processes 500 and 600, as described herein. The processes 500, and 600 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

A. Process for Forming CRE

FIG. 5 is a flow chart illustrating an example process 500 for forming a CRE (e.g., CRE 100 of FIG. 1), according to embodiments. In some embodiments, multiple CREs may be formed via the process disclosed herein, for example an array of CREs. In some embodiments, forming the CRE may involve forming one or more parts of the CRE, such as the recording surfaces (e.g., electrodes 104 of FIG. 1), either separately or jointly. In an exemplary embodiment, at block 505, forming process 500 may include forming a central electrode (e.g., electrode 104a of FIG. 1) on a non-conductive or insulating substrate (e.g., electrode substrate 102 of FIG. 1). The substrate may be rigid (e.g., gold-plated copper on biocompatible dielectric) or flexible (e.g., polyester film, or silver paste on polyester film) in order to be mounted and/or contact a monitoring target, such as a patient. In some embodiments, the substrate may be designed to provide a consistent contact potential with the target, as well as to fit the target's form. In particular, flexible substrates may improve the CRE's ability to adjust to body contours for better contact and to provide higher signal amplitude and signal-to-noise ratio. In various embodiments, the CRE may be biocompatible, wireless, battery-powered, and/or disposable. The central electrode (e.g., central electrode 104a of FIG. 1), may be circularly symmetric, and, as such, may be or include a disc or a ring.

At block 510, the process 500 may include forming a middle electrode on the substrate (e.g., electrode 104b of FIG. 1). In some examples, this may include depositing, printing, and/or securing the middle electrode to the substrate. In various embodiments, the middle electrode may be pre-formed, or may be formed on the electrode substrate as part of the forming process. For example, the central electrode and middle electrode of the CRE may be printed via screen printing, inkjet, and/or gravure techniques onto the electrode substrate.

At block 515, the process 500 may optionally include forming one or more additional middle electrodes (e.g., electrode 104c of FIG. 1). Similarly to the operations of block 510, block 515 may include forming one or more additional middle electrodes by disposing pre-formed electrodes concentric with the middle electrode and the central electrode. When printing or engraving the electrodes, however, block 505, block 510, and block 515 may occur together, such that portions of the concentric electrodes and the central electrode may be formed concurrently. In this way, the process 500 may also include block 520, where an outer electrode (e.g., electrode 104d of FIG. 1) may be formed on the electrode substrate. As with block 515, the outer electrode may be pre-formed and disposed on the electrode substrate, in which case the outer electrode may be formed concurrently with or separately from the other electrodes of the CRE. Similarly, when the process 500 includes printing or engraving to form the electrodes, the block 520 may be concurrent with the block 505, block 510, and block 515, as when the electrodes are formed by patterning a substrate, followed by selective deposition of a metal film onto regions of the substrate to form the electrodes.

The electrodes may be formed such that the central electrode is circular and had a radius of R. In such cases, the middle electrode may be a ring electrode, and have an inner radius of 2R and an outer radius of 3R. In such cases the outer electrode may also be a ring electrode and may have an inner radius of 4R and an outer radius of 9R. In some examples, the middle electrode may be narrower than the outer electrode. In some examples, the outer electrode may be wider than the radius of the central electrode, R. In some examples, the middle electrode may be closer to the central electrode than to the outer electrode, which may be measured by a smaller inter-electrode spacing between the central electrode and the middle electrode than between the middle and the outer electrodes. In some examples, the outer electrode, the middle electrode, and the central electrode may include an electrode surface area covering more than 50% of an active area (e.g., active area 106 of FIG. 1) of the electrode substrate. The outer electrode may cover more than 25% of the active area of the electrode substrate.

At block 525, the process may optionally include electrically connecting the electrodes with terminals to connect the CRE to an interface, such as an interface to systems 400 or 450 in FIGS. 4A and 4B. For example, the terminals may be separate leads (e.g., leads 110 of FIG. 1) that can be plugged into an active device (e.g., controller 402 of FIG. 4A). In various embodiments, one or more electrodes may be shorted together, thereby providing a "quasi-CRE" configuration of a lower number of recording sites. For example, a tripolar CRE (e.g., CRE 100 of FIG. 1) with the two electrodes shorted together may be referred to as a quasi-bipolar CRE. In some embodiments, the CRE configuration may be optimized by combining signals from all the recording surfaces into a Laplacian estimate. Such an approach may result in higher Laplacian estimation accuracy and radial attenuation.

B. Process for Determining Functional of Potential

FIG. 6 is a flow chart illustrating an example process 600 for determining a functional of an electrostatic potential measurable by a CRE (e.g., CRE 100 of FIG. 1), according to some embodiments. Process 600 may be performed in a system such as system 800 of the example of FIG. 8 or computing device 404 of FIG. 4B, for example, in coordination with one or more operations of process 700 of FIG. 7, below.

At block 610, the system may receive information specifying a geometrical configuration of the CRE. In a typical example, this may include a number n of electrodes excluding the central electrode (e.g., rings) in the CRE and/or the radii and widths of the electrodes. In some embodiments, the inter-electrode spacings may be non-uniform.

At block 620, the system may determine a set of coefficients for Laplacian estimation associated with a series expansion of the electrostatic potential for the geometrical configuration of the CRE. The system may calculate potentials on all recording surfaces using a series expansion of the electrostatic potential for the geometrical configuration. The potentials may be converted to potential differences of the form "ring minus disc", by calculating a difference between the potential on an electrode (e.g., the middle electrode, the outer electrode, etc.) and the central electrode. The potential differences may be combined into a system of equations, for which the solutions are coefficients that allow cancellation of truncation terms in the Taylor series expansion up to the order of 2n, where "n" is the number of electrodes excluding the central electrode.

Determining the coefficients for Laplacian estimation may be based on a cancellation of at least a first truncation term of the series expansion of the electrostatic potential measured by the CRE. Specifically, the choice of coefficients may result in the cancellation of the first truncation term. In an embodiment, the coefficients are chosen based on this cancellation. The first truncation term may have an order 2n. In an embodiment, the system may cancel multiple truncation terms. Typically, this may include n−1 truncation terms of even order, up to the order of 2n.

The system may determine a set of coefficients including at least a first and a second coefficient corresponding to respective electrodes of the CRE. For example, for a tripolar CRE (e.g., CRE 303 of FIG. 3C), the coefficients determined may be substantially equal to 952/1227 for the difference of the inner electrode's potential from the central electrode potential, and −6/409 for the difference of the outer electrode's potential from the central electrode potential (equivalent to −53 and −1 for a preamplifier configured for integer coefficients). In various embodiments, the first coefficient is between −60 and −10 times the second coefficient, between −70 and −10 times the second coefficient, or between −80 and −10 times the second coefficient, or may fall within a broader range less than −10 times the second coefficient. In order to use all the information measured by the electrodes of the TCRE, both coefficients may be non-zero.

At block 630, the system may estimate a dependence of the Laplacian on a set of potential differences, including at least a first and a second potential difference corresponding to respective electrodes of the CRE. In an embodiment, the system can estimate a dependence of a different functional. In an embodiment, the estimated dependence of the Laplacian may involve a linear combination of the set of potential differences, wherein a respective potential difference is multiplied by a respective coefficient of the set of coefficients.

In some embodiments, the system can further transmit instructions to configure an electrophysiological monitoring system based on the determined set of coefficients. In an embodiment, the system may include an amplification device configured to combine the potential differences measured by the CRE based on the determined coefficients. For example, the system may use a custom preamplifier board to calculate the Laplacian, and this Laplacian estimate may be sent to the clinical amplifier for each CRE.

C. Process of Recording Electrophysiological Signals

Figure 7:
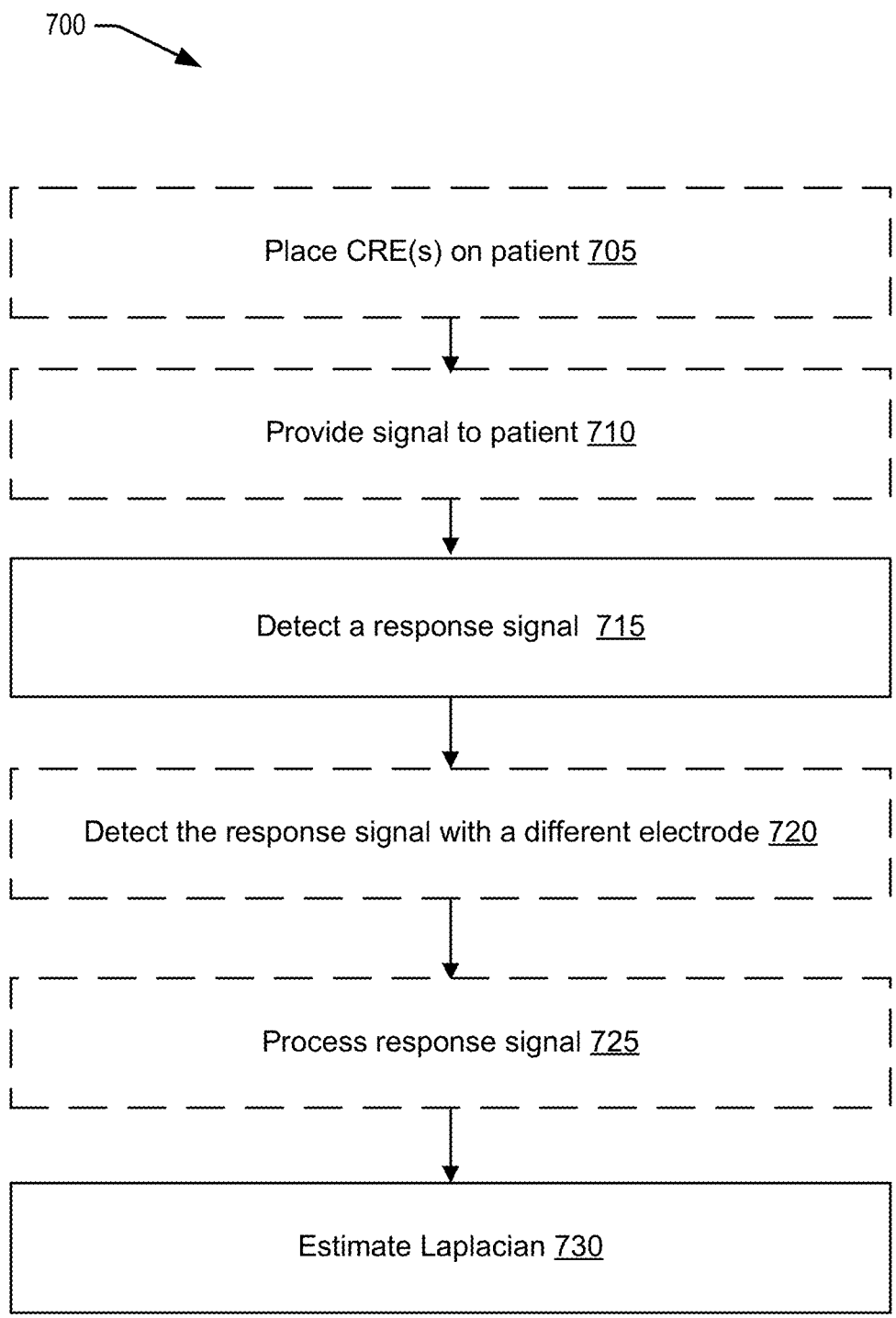
FIG. 7 is a flow chart illustrating an example process for measuring a response signal by a CRE using a clinical system, in accordance with some embodiments.

FIG. 7 is a flow chart illustrating an example process 700 for measuring a response signal by a CRE (e.g., CRE 100 of FIG. 1) using a clinical system (e.g., system 400 of FIG. 4), in accordance with some embodiments. As described in reference to FIG. 4A, a system may be configured for electrophysiological measurement of a patient, including, but not limited to seizure monitoring, EEG, ECG, etc. For example, process 700 may optionally include block 705 at which one or more CREs may be placed at a number of positions on the patient. The placement may be localized to a specific region of the patient, such as overlying a specific nerve or organ, or may be distributed in an array on a broad region, such as the scalp or the abdomen.

At block 710, the system may optionally provide a signal to a CRE or to multiple CREs arranged in an array. The signal provided to the patient may be a monitoring signal or a stimulation signal, EEG, brain-computer interface signals, seizure onset detection, detection of high-frequency oscillations and seizure onset zones, as well as signals implemented in applications involving electroenterograms, ECGs, electrohysterograms, or any other kind of electrophysiological monitoring.

At block 715, the system may detect a response signal. Response signals may be measured as potentials at one or more electrodes of the CRE, and may be generated by physiological processes of the patient (e.g., patient 408 of FIG. 4A). The response signals may be generated in response to electrical signals from a controller of the system (e.g., controller 402 of FIG. 4A). Optionally, at block 720, the response signal may be measured at a different electrode than the electrode used to provide the monitoring or stimulation signal to the patient at block 710. For example, in the context of the CRE 100 of FIG. 1, the signal may be provided to the patient between the outer electrode 104d and the central electrode 104a, while a second CRE may be positioned near the CRE 100 to record the response signal. In some example, the response signal may be measured by one or more of the middle electrodes 104b-c. Optionally, at block 725 the response signal may be passed by the controller 402, which may perform some filtering and/or processing, to a computing device of the system (e.g., computing device 404 of FIG. 4A).

At block 730, the response signal may optionally be used to estimate a Laplacian. As described in more detail in reference to FIG. 6, a CRE or an array of CREs may measure the surface Laplacian, or the second spatial derivative, of the electrostatic potential on a surface of the patient. In some embodiments, the process of estimating the Laplacian may include applying linear combination coefficients for the potentials measured by the CRE. For example, an amplifier or preamplifier (e.g., amplifier or preamplifier 464 of FIG. 4B) included in or associated with the controller may be configured to calculate a Laplacian estimate from the potentials measured at block 715, using the coefficients.

V. ADDITIONAL CONSIDERATIONS

Figure 8:
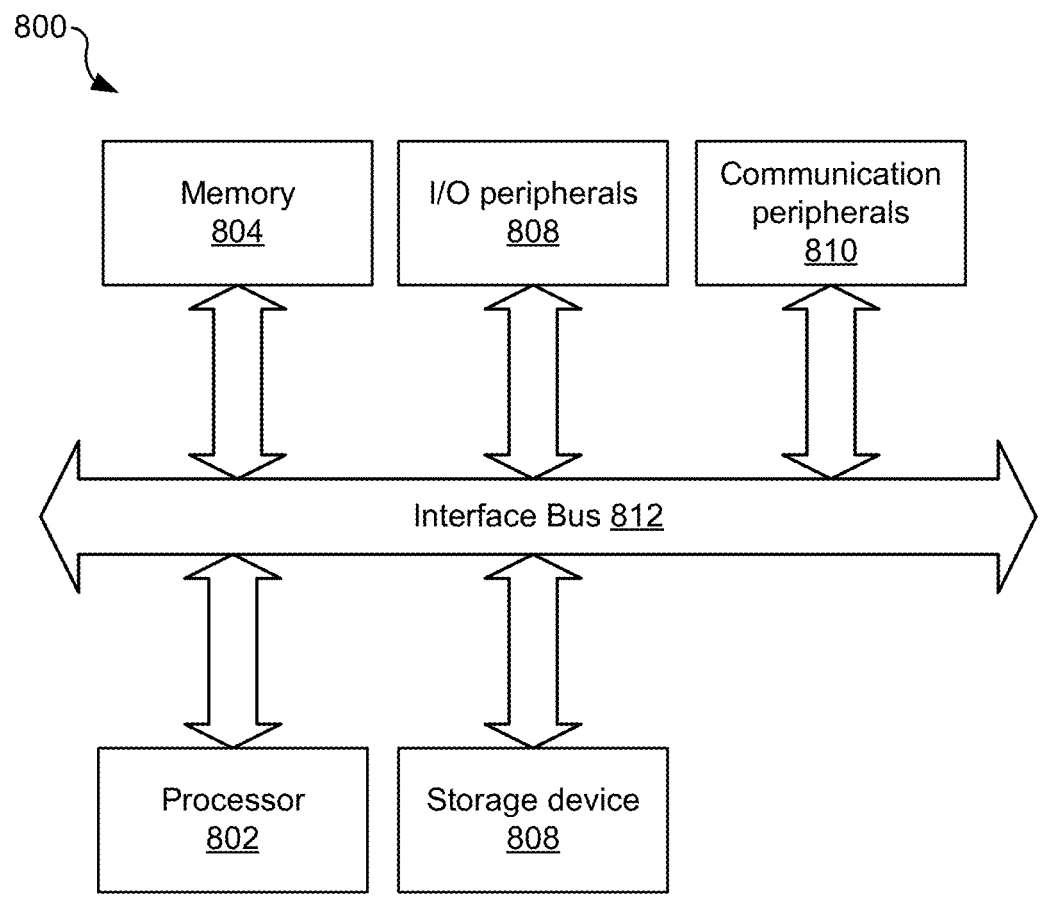
FIG. 8 illustrates examples of components of a computer system, in accordance with some embodiments.

FIG. 8 illustrates examples of components of a computer system 800, according to at least one example. The computer system 800 may be a single computer such as a user computing device and/or can represent a distributed computing system such as one or more server computing devices.

The computer system 800 may include at least a processor 802, a memory 804, a storage device 806, input/output peripherals (I/O) 808, communication peripherals 810, and an interface bus 812. The interface bus 812 is configured to communicate, transmit, and transfer data, controls, and commands among the various components of the computer system 800. The memory 804 and the storage device 806 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example FLASH® memory, and other tangible storage media. Any of such computer-readable storage media can be configured to store instructions or program codes embodying aspects of the disclosure. The memory 804 and the storage device 806 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 800.

Further, the memory 804 includes an operating system, programs, and applications. The processor 802 is configured to execute the stored instructions and includes, for example, a logical processing unit, a microprocessor, a digital signal processor, and other processors. The memory 804 and/or the processor 802 can be virtualized and can be hosted within another computing system of, for example, a cloud network or a data center. The I/O peripherals 808 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 808 are connected to the processor 802 through any of the ports coupled to the interface bus 812. The communication peripherals 810 are configured to facilitate communication between the computer system 800 and other computing devices over a communications network and include, for example, a network interface controller, modem, wireless and wired interface cards, antenna, and other communication peripherals.

In some embodiments, the system and methods described herein can determine a functional of an electrostatic potential, the electrostatic potential measurable by CRE comprising at least a middle electrode and an outer electrode, the middle electrode and the outer electrode concentric with a central electrode. The system may receive information specifying a geometrical configuration of the CRE. The system may then estimate a dependence of the functional on a set of potential differences comprising at least a first potential difference corresponding to the middle electrode and a second potential difference corresponding to the outer electrode, by at least determining a set of coefficients for Laplacian estimation associated with a series expansion of the electrostatic potential for the geometrical configuration. Estimating the dependence of the functional on a set of potential differences may further include determining a set of coefficients for the dependence, the set of coefficients comprising at least a nonzero first coefficient of the first potential difference and a nonzero second coefficient of the second potential difference, wherein the first coefficient is between −60 and −10 times the second coefficient, between −70 and −10 times the second coefficient, between −80 and −10 times the second coefficient, or a wider range, for a TCRE.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. An electrode device for electrophysiological measurement, the electrode device comprising:
    an electrode substrate having a surface area;
    a central disc electrode disposed on the electrode substrate and covering a central portion of the surface area, the central disc electrode having a first radius, "R," of the central disc electrode relative to a center point of the central disc electrode;
    a middle ring electrode concentric with the central disc electrode, the middle ring electrode covering a first portion of the surface area of the electrode substrate between a second radius and a third radius from the center point, the second radius being greater than the first radius; and
    an outer ring electrode concentric with the central disc electrode and the middle ring electrode, the outer ring electrode covering a second portion of the surface area of the electrode substrate between a fourth radius and a fifth radius from the center point, the fourth radius being greater than the third radius and the fifth radius defining an active area of the electrode substrate,
    wherein a first distance between the fourth radius and the fifth radius is greater than both a second distance between the second radius and the third radius and R, and
    wherein values of R, the first distance, and the second distance are selected to increase accuracy of a surface Laplacian estimate signal recordable via the electrode device using a finite dimensions model.

2. The electrode device of claim 1, wherein the central portion, the first portion, and the second portion together cover more than 50% of the active area of the electrode substrate.

3. The electrode device of claim 1, wherein the second portion covers more than 25% of the active area of the electrode substrate.

4. The electrode device of claim 1, wherein the second radius is 2R, the third radius is 3R, the fourth radius is 4R, and the fifth radius is 9R.

5. The electrode device of claim 1, wherein the middle ring electrode is a first middle ring electrode, the electrode device further comprising:
    a second middle ring electrode concentric with the central disc electrode, the second middle ring electrode disposed on the electrode substrate covering a third portion of the surface area between a sixth radius and a seventh radius from the center point, wherein the seventh radius is smaller than the fourth radius and the sixth radius is greater than the third radius.

6. The electrode device of claim 5, wherein:
    the first distance is greater than a third distance between the sixth radius and the seventh radius;
    the first distance is greater than the third distance and the third distance is greater than the second distance;
    the third distance is greater than the second distance and R;
    the second distance is greater than R; or
    the third distance is greater than R.

7. The electrode device of claim 1, wherein the selected values of R, the first distance, and the second distance correspond to parameters of the finite dimensions model, the selected values determined by the parameters that provide a lowest truncation error of a calculated surface Laplacian estimate.

8. The electrode device of claim 1, wherein the selected values of R, the first distance, and the second distance increase the accuracy of the surface Laplacian estimate signal compared to a second surface Laplacian estimate signal recordable by a different electrode device configured using a negligible dimensions model.

9. An electrode device for electrophysiological measurement, the electrode device comprising:
    an electrode substrate having a surface area;
    a central electrode disposed on the electrode substrate around a central portion of the surface area; and
    a plurality of electrodes disposed on the electrode substrate concentric with the central electrode, the plurality of electrodes comprising:
        a first electrode covering a first portion of the surface area of the electrode substrate; and
        a second electrode covering a second portion of the surface area of the electrode substrate,
    wherein the second portion is greater than a combined surface area of the first portion and the central portion by at least 45%, and wherein the central portion, the first portion, and the second portion are selected to increase accuracy of a surface Laplacian estimate signal recordable via the electrode device using a finite dimensions model.

10. The electrode device of claim 9, wherein:
    the surface area of the electrode substrate extends to an outer periphery of the second electrode;
    and the central portion and the plurality of electrodes together cover more than 50% of the surface area of the electrode substrate.

11. The electrode device of claim 9, wherein:
    the surface area of the electrode substrate extends to an outer periphery of the second electrode; and
    the second portion covers more than 25% of the surface area of the electrode substrate.

12. The electrode device of claim 9, wherein the central electrode comprises a disc covering a central region of the electrode substrate.

13. The electrode device of claim 9, wherein a first distance between the first electrode and the second electrode is greater than a distance between the central electrode and the first electrode.

14. The electrode device of claim 9, further comprising a third electrode concentric with the central electrode and the first electrode, the third electrode covering a third portion of the surface area of the electrode substrate and disposed on the electrode substrate between the first electrode and the second electrode.

15. A method of forming an electrode device, the method comprising:
- forming a central electrode on an electrode substrate, the central electrode having a first radius, "R" relative to a center point of the central electrode;
- forming a middle electrode on the electrode substrate concentric with the central electrode, the middle electrode disposed on the electrode substrate between a second radius and a third radius from the center point, the second radius being greater than the first radius; and
- forming an outer electrode on the electrode substrate concentric with the central electrode and the middle electrode, the outer electrode disposed on the electrode substrate between a fourth radius and a fifth radius from the center point, the fourth radius being larger than the third radius,
- wherein a first distance between the fourth radius and the fifth radius is greater than both a second distance between the second radius and the third radius and R, and
- wherein values of R, the first distance, and the second distance are selected to increase accuracy of a surface Laplacian estimate signal recordable via the electrode device using a finite dimensions model.

16. The method of claim 15, wherein the outer electrode, the middle electrode, and the central electrode comprise an electrode surface area covering more than 50% of an active area of the electrode substrate.

17. The method of claim 15, wherein the outer electrode covers more than 25% of the active area of the electrode substrate.

18. The method of claim 15, wherein the second radius is 2R, the third radius is 3R, the fourth radius is 4R, and the fifth radius is 9R.

19. The method of claim 15, wherein a distance between the middle electrode and the outer electrode is greater than a distance between the central electrode and the middle electrode.

20. The method of claim 15, wherein the middle electrode is a first middle electrode, the method further comprising:
- forming a second middle electrode on the electrode substrate concentric with the central electrode, the second middle electrode disposed on the electrode substrate between a sixth radius and a seventh radius from the center point, wherein the seventh radius is smaller than the fourth radius.

* * * * *